United States Patent [19]

Gough

[11] 4,364,767

[45] Dec. 21, 1982

[54] N(CARBOXYMETHYL-N-(PHOSPHONOMETHYL)-5-(2-CHLORO-4-TRIFLUOROMETHYL PHENOXY)-2-NITROBENZAMIDE AND SALTS THEREOF

[75] Inventor: Stanley T. D. Gough, Whitehouse Station, N.J.

[73] Assignee: Rhone-Poulenc Agrochimie, Lyons, France

[21] Appl. No.: 286,995

[22] Filed: Jul. 27, 1981

[51] Int. Cl.$^3$ .......................... A01N 9/36; C07F 9/38; C07F 9/02; C07F 9/06

[52] U.S. Cl. .................................. 71/86; 260/501.12; 260/502.5 D; 544/232; 546/24

[58] Field of Search ....................... 260/502.5, 501.12; 71/86; 544/232; 546/24

[56] References Cited

U.S. PATENT DOCUMENTS

| | | | |
|---|---|---|---|
| 3,970,695 | 7/1976 | Rueppel | ............................ 260/502.5 |
| 4,197,254 | 4/1980 | Gaertner | ............................ 260/502.5 |

*Primary Examiner*—Joseph E. Evans
*Attorney, Agent, or Firm*—Morgan, Finnegan, Pine, Foley & Lee

[57] ABSTRACT

There are provided N(carboxymethyl-N-(phosphonomethyl)-5-(2-chloro-4-trifluoromethyl phenoxy)-2-nitrobenzamide and salts thereof.

4 Claims, No Drawings

N(CARBOXYMETHYL-N-(PHOSPHONOMETHYL)-5-(2-CHLORO-4-TRIFLUOROMETHYL PHENOXY)-2-NITROBENZAMIDE AND SALTS THEREOF

CROSS-REFERENCE TO RELATED APPLICATIONS:

This application is a related to of U.S. application Ser. No. 282,316, filed July 10, 1981, which, in turn, is a continuation-in-part of U.S. application Ser. No. 117,732, filed Feb. 1, 1980.

BACKGROUND OF THE INVENTION

Herbicidal 5-[2-chloro-4-(trifluoromethyl)phenoxy]-2-nitrobenzoic acid and salts thereof, and various herbicidal derivatives of these compounds have been proposed including alkyl and cycloalkyl esters, alkylthio esters, phenyl ester, alkyl and dialkyl amido and benzoyl chloride forms. U.S. Pats. which describe such compounds and the like include Nos. 3,652,645; 3,784,635; 3,873,302; 3,983,168; 3,907,866; 3,798,276; 3,928,416; and 4,063,929.

SUMMARY OF THE INVENTION

This invention provides certain herbicidal compounds of the formula:

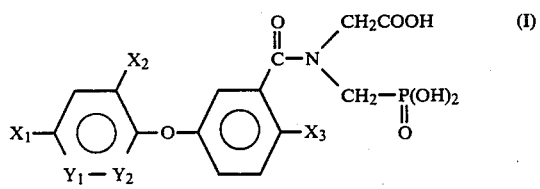

where:
(i) $Y_1$ is N or C—H;
(ii) $Y_2$ is N or C—$X_4$, provided that $Y_1$ is not N when $Y_2$ is C—$X_4$; and
(iii) $X_1$, $X_2$, $X_3$ and $X_4$ are groups which are capable of being incorporated into formula I and which collectively impart herbicidal activity thereto.

The invention also provides agronomically acceptable salts (e.g., alkali metal salts such as sodium salts or ammonium salts of the formula $(C_1-C_6\ alkyl)_nNH_{4-n}$, where n is 0–4) of compounds according to formula I.

Preferred compounds according to the present invention are:

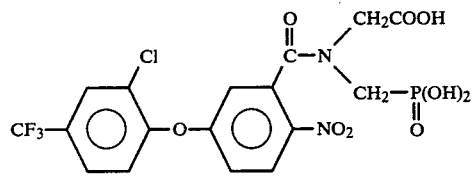

and the sodium salts thereof.

EXAMPLE

Preparation of N-(carboxymethyl-N-(phosphonomethyl)-5-(2-chloro-4-trifluoromethyl phenoxy)-2-nitrobenzamide.

N(phosphonomethyl)-glycine (1.7 g) is dissolved in excess 10% sodium hydroxide solution. 5-(2-chloro-4-trifluoromethyl-phenoxy)-2-nitro-benzoyl chloride (3.8 g) is then added and the mixture shaken vigorously overnight. The mixture is then filtered and the filtrate acidified to give the product.

The compounds of formula I may be prepared by

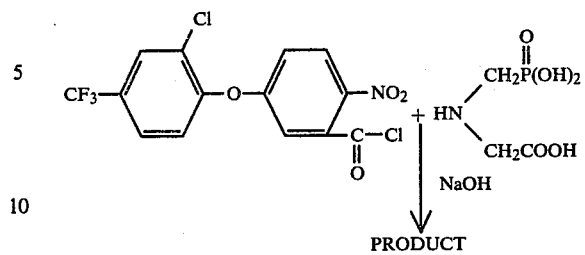

The compounds of this invention can be applied in various ways to achieve herbicidal action. They can be applied per se, but may be applied as the toxic components in pesticidal compositions of the compound and a carrier. These compositions may be applied directly to the soil and often incorporated therewith. The compositions can be applied as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth. gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil. In practice, herbicidal application is measured in terms of pounds of herbicide applied per acre. The compounds of this invention are effective herbicides when applied in herbicidal amounts, e.g., at rates between about 0.03 pound and about 10 pounds per acre.

What is claimed is:

1. A herbicidal compound of the formula

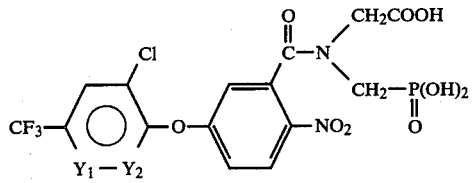

where $Y_1$ is N or C—H, $Y_2$ is N or C—H provided that $Y_1$ is not N when $Y_2$ is C—H and agronomically acceptable salts thereof.

2. A compound according to claim 1 selected from the group consisting of

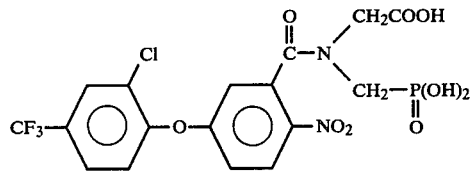

and the sodium salts thereof.

3. A herbicidal composition comprising a compound according to claim 1 and an agronomically acceptable carrier.

4. A method for combating unwanted plants which comprises contacting them with a herbicidally effective amount of a compound according to claim 1.

* * * * *